US011890248B2

(12) United States Patent
Lee et al.

(10) Patent No.: US 11,890,248 B2
(45) Date of Patent: Feb. 6, 2024

(54) THERMOTHERAPY DEVICE AND CONTROL METHOD THEREFOR

(71) Applicant: CERAGEM CO., LTD, Cheonan-si (KR)

(72) Inventors: Dong Myoung Lee, Asan-si (KR); Ki Sung Kim, Cheonan-si (KR); Sang Cheol Han, Cheonan-si (KR); Jin Cheol Park, Cheonan-si (KR)

(73) Assignee: CERAGEM CO., LTD., Cheonan-si (KR)

( * ) Notice: Subject to any disclaimer, the term of this patent is extended or adjusted under 35 U.S.C. 154(b) by 255 days.

(21) Appl. No.: 16/334,270

(22) PCT Filed: Jan. 12, 2018

(86) PCT No.: PCT/KR2018/000606
§ 371 (c)(1),
(2) Date: Mar. 18, 2019

(87) PCT Pub. No.: WO2018/186565
PCT Pub. Date: Oct. 11, 2018

(65) Prior Publication Data
US 2019/0216680 A1 Jul. 18, 2019

(30) Foreign Application Priority Data
Apr. 7, 2017 (KR) .................... 10-2017-0045132

(51) Int. Cl.
*A61H 15/02* (2006.01)
*A61F 7/00* (2006.01)
(Continued)

(52) U.S. Cl.
CPC ............... *A61H 15/02* (2013.01); *A61F 7/00* (2013.01); *A61F 7/007* (2013.01); *A61H 1/00* (2013.01);
(Continued)

(58) Field of Classification Search
CPC ............ A61G 2203/32; A61G 2203/34; A61G 2203/44; A47C 7/72; B60N 2/976
See application file for complete search history.

(56) References Cited

U.S. PATENT DOCUMENTS 4,586,493 A * 5/1986 Goodman ................. A61H 1/00
601/116
5,155,685 A * 10/1992 Kishi ....................... B60N 2/66
318/467
(Continued)

FOREIGN PATENT DOCUMENTS

CN 2928089 8/2007
CN 202761641 3/2013
(Continued)

OTHER PUBLICATIONS

Office Action issued in Corresponding Korean Application No. 10-2019-0176113, dated Jun. 25, 2020 (Korean, No English Translation provided).
(Continued)

*Primary Examiner* — Bradley H Philips
*Assistant Examiner* — Savannah L Gabriel
(74) *Attorney, Agent, or Firm* — NORTON ROSE FULBRIGHT US LLP

(57) ABSTRACT

An apparatus including a thermal ceramic module including a body, a first supporting plate located on the body, a second supporting plate located on the first plate, an ascending and descending driving part coupled to a lower portion of the first plate and configured to move the first plate in a vertical direction on the basis of the body, and a ceramic member coupled to the second plate; a weight sensor provided on a lower surface of the second plate to sense a body pressure of a user; and a controller configured to control a massage mode of the thermal ceramic module, wherein the controller controls a driving height of the ascending and descending
(Continued)

driving part according to the body pressure of the user sensed by the weight sensor to provide the same pressure to the user through the ceramic member on the basis of a predetermined desired intensity.

10 Claims, 9 Drawing Sheets

(51) Int. Cl.
*A61H 15/00* (2006.01)
*A61H 7/00* (2006.01)
*A61H 1/00* (2006.01)
*A61N 5/06* (2006.01)

(52) U.S. Cl.
CPC ............... *A61H 7/00* (2013.01); *A61H 15/00* (2013.01); *A61H 15/0078* (2013.01); *A61F 2007/0011* (2013.01); *A61F 2007/0024* (2013.01); *A61H 2015/0021* (2013.01); *A61H 2201/0207* (2013.01); *A61H 2201/1669* (2013.01); *A61H 2201/5071* (2013.01); *A61N 5/0625* (2013.01)

(56) References Cited

U.S. PATENT DOCUMENTS

| | | | | |
|---|---|---|---|---|
| 5,792,080 | A * | 8/1998 | Ookawa | A61H 1/00 601/102 |
| 6,117,094 | A * | 9/2000 | Fujii | A61H 15/00 601/102 |
| 2003/0212352 | A1 | 11/2003 | Kahn | |
| 2004/0034314 | A1* | 2/2004 | Kobayashi | B60N 2/99 601/5 |
| 2004/0245036 | A1 | 12/2004 | Fujita et al. | |
| 2004/0260215 | A1 | 12/2004 | Kim | |
| 2005/0015029 | A1* | 1/2005 | Kim | A61H 15/02 601/99 |
| 2010/0210921 | A1 | 8/2010 | Park et al. | |
| 2013/0110007 | A1* | 5/2013 | Jeon | A61B 5/4566 600/594 |
| 2013/0253390 | A1* | 9/2013 | Park | A61H 15/02 601/99 |
| 2014/0371638 | A1 | 12/2014 | Lee et al. | |
| 2016/0000647 | A1* | 1/2016 | Eberhardt | A61H 23/0254 601/70 |
| 2017/0043681 | A1* | 2/2017 | Seiller | B60N 2/0248 |
| 2018/0110960 | A1 | 4/2018 | Youngblood et al. | |
| 2019/0209843 | A1 | 7/2019 | Park et al. | |

FOREIGN PATENT DOCUMENTS

| | | | |
|---|---|---|---|
| CN | 104434485 | 3/2015 | |
| JP | H0531146 A | 2/1993 | |
| JP | H09-154905 | 6/1997 | |
| JP | 3572128 B2 * | 9/2004 | ............ A61H 15/00 |
| JP | 2007325712 A | 12/2007 | |
| JP | 2010131117 | 6/2010 | |
| JP | 2013005899 | 1/2013 | |
| KR | 20030063775 | 7/2003 | |
| KR | 2012-0001602 | 1/2012 | |
| KR | 10-2012-0118398 | 10/2012 | |
| KR | 2012-0122420 | 11/2012 | |
| KR | 2014-0079717 | 6/2014 | |
| KR | 2016-0083265 | 7/2016 | |
| RU | 106112 | 7/2011 | |
| WO | WO-02069880 A1 * | 9/2002 | ............ A61H 39/00 |
| WO | WO 2002069880 | 9/2002 | |
| WO | WO 2015083967 | 6/2015 | |

OTHER PUBLICATIONS

Search Report issued in Corresponding Russian Application No. 2019134166, dated Apr. 21, 2020 (Russian, No English Translation provided).
Extended European Search Report issued in Corresponding European Application No. 187804018, dated Oct. 29, 2020.
Search Report issued in Corresponding Chilean Application No. 2849-2019, dated Sep. 29, 2020 (No English Translation provided).
International Search Report and Written Opinion issued in International Patent Application No. PCT/KR2018/000606, dated May 8, 2018.
Office Action issued in corresponding Japanese Application No. 2019-554793, dated Jun. 25, 2021. (Japanese)
Hearing Notice issued in the corresponding Indian Application No. 201814003885, dated Dec. 8, 2023.

* cited by examiner

THERMOTHERAPY DEVICE AND CONTROL METHOD THEREFOR

CROSS-REFERENCE TO RELATED APPLICATIONS

This application is a national phase application under 35 U.S.C. § 371 of International Application No. PCT/KR2018/000606, filed Jan. 12, 2018, which claims priority to and the benefit of Korean Patent Application No. 10-2017-0045132, filed Apr. 7, 2017. The contents of the referenced patent applications are incorporated into the present application by reference.

FIELD OF THE DISCLOSURE

The present invention relates to a thermo-therapeutic apparatus and a method for controlling the same, and more particularly, a thermo-therapeutic apparatus capable of providing a desired intensity of massage at the same pressure using a weight sensor according to a body part or a user and a method for controlling the same.

DESCRIPTION OF RELATED ART

When continuously working for a long time with not only an improper posture but also a steady posture, such as looking at a computer monitor for a long time, or using a smartphone for a long time, acute or chronic pains occur in muscles and nerves in a cervical region. A thermo-therapeutic apparatus is used for improving blood circulation or relieving the pains in the muscles by applying stimulation to a part in which the pains occur through thermal massage.

In the thermo-therapeutic apparatus, a massage intensity is determined by a pressure according to an ascending and descending height of a ceramic member configured to come into contact with a body. As an example, the thermo-therapeutic apparatus provides a greater pressure when the ceramic member ascends and thus the massage intensity increases, and provides a smaller pressure when the ceramic member descends and thus the massage intensity decreases.

However, in the conventional thermo-therapeutic apparatus, since the ascending and descending height of the ceramic member is uniform at a set massage intensity, a pressure applied to each body part can be different according to a body type of the user. Accordingly, since the massage intensity to each body part is felt to be different by the user, strictly the same massage intensity cannot be provided.

Further, the massage intensity set to be the same is felt differently by the user for each body part, and when the effect is severe, pain occurs or a massage effect is reduced.

SUMMARY OF THE INVENTION

To solve a problem of the conventional technology, one embodiment of the present invention provides a thermo-therapeutic apparatus configured to provide the same pressure to each user or each body part of a user in a particular massage intensity, and a method for controlling the same.

Further, the present invention provides a thermo-therapeutic apparatus configured to recognize a user by body pressure distribution and a body type of the user and automatically control setting and performance of massage, and a method for controlling the same.

One aspect of the present invention provides a thermo-therapeutic apparatus including a thermal ceramic module which includes a body, a first supporting plate located on the body, a second supporting plate located on the first supporting plate, an ascending and descending driving part coupled to a lower portion of the first supporting plate and configured to move the first supporting plate in a vertical direction on the basis of the body, and a ceramic member coupled to the second supporting plate; a weight sensor provided on a lower surface of the second supporting plate to sense a body pressure of a user; and a controller configured to control setting and performance of a massage mode of the thermal ceramic module, wherein the controller controls a driving height of the ascending and descending driving part according to the body pressure of the user sensed by the weight sensor to provide the same pressure to the user through the ceramic member on the basis of a predetermined desired intensity.

The thermo-therapeutic apparatus may further include a storage part in which reference height information of the ascending and descending driving part is stored according to the desired intensity, wherein the controller may calculate driving height adjustment information according to the body pressure sensed on the basis of the reference height information to store the driving height adjustment information in the storage part and control the driving height of the ascending and descending driving part with reference to the driving height adjustment information according to the body pressure sensed by the weight sensor.

The controller may determine whether a predetermined time passes without a predetermined change of the pressure after the weight sensor senses a pressure greater than or equal to a first reference pressure and control the thermal ceramic module so that the massage mode is automatically started when the predetermined time passes.

The controller may determine whether a predetermined time passes after the weight sensor senses a pressure lower than or equal to a second reference pressure while the massage mode is performed and control the thermal ceramic module so that the massage mode is automatically paused when the predetermined time passes.

The controller may determine whether the predetermined time passes after the massage mode is paused, and control the thermal ceramic module so that the massage mode is automatically ended when the predetermined time passes.

The thermo-therapeutic apparatus may further include a storage part in which user specific information including a body type, a weight, and massage mode setting information of the user is stored, wherein the controller may store current massage mode setting information in the storage part as the user specific information when the massage mode of the thermal ceramic module is ended.

The thermo-therapeutic apparatus may further include a horizontal conveying motor configured to horizontally drive the thermal ceramic module; and a storage part configured to store body type information corresponding to at least one of body pressure distribution and a current variation amount of the horizontal conveying motor, wherein the controller may determine the body type of the user with reference to the body type information according to at least one of body pressure distribution of the user on the basis of a sensing result sensed by the weight sensor for a body part, and a current variation amount of the horizontal conveying motor according to a location.

The user specific information including the body type, the weight, and the massage mode setting information of the user may be stored in the storage part, and the controller may recognize the user with reference to the user specific information according to the determined body type of the user and automatically set the massage mode of the thermal ceramic module according to the massage mode setting information of the recognized user.

Another aspect of the present invention provides a method for controlling a thermo-therapeutic apparatus including setting a massage mode of a thermal ceramic module including a body, a first supporting plate located on the body, a second supporting plate located on the first supporting plate, an ascending and descending driving part coupled to a lower portion of the second supporting plate and configured to move the first supporting plate in a vertical direction on the basis of the body, and a ceramic member coupled to the second supporting plate; sensing a body pressure of a user through a weight sensor provided on a lower surface of the second supporting plate; and controlling performance of the massage mode of the thermal ceramic module, wherein a driving height of the ascending and descending driving part is controlled according to the body pressure of the user sensed by the weight sensor to provide the same pressure to the user through the ceramic member on the basis of a predetermined desired intensity.

The method for controlling a thermo-therapeutic apparatus may further include providing reference height information of the ascending and descending driving part according to the desired intensity, wherein the controlling may include calculating driving height adjustment information according to the body pressure sensed on the basis of the reference height information and controlling the driving height of the ascending and descending driving part with reference to the driving height adjustment information according to the body pressure sensed by the weight sensor.

The method for controlling a thermo-therapeutic apparatus may further include a first determining operation which determines whether a predetermined time passes without a predetermined change of the pressure after the weight sensor senses a pressure greater than or equal to a first reference pressure; automatically starting the massage mode of the thermal ceramic module when the predetermined time passes; a second determining operation which determines whether a predetermined time passes after the weight sensor senses a pressure lower than or equal to a second reference pressure while the massage mode is performed; automatically pausing the massage mode of the thermal ceramic module when the predetermined time passes; a third determining operation which determines whether a predetermined time passes after the massage mode is paused; and automatically ending the massage mode of the thermal ceramic module when the predetermined time passes.

The method for controlling a thermo-therapeutic apparatus may further include providing body type information corresponding to at least one of body pressure distribution and a current variation amount of a horizontal conveying motor configured to horizontally drive the thermal ceramic module; sensing at least one of a body pressure for a body part of the user and a current change of the horizontal conveying motor according to a location; determining a body type of the user with reference to the body type information according to at least one of body pressure distribution of the user on the basis of a sensing result sensed by the weight sensor and a current variation amount of the horizontal conveying motor according to a location; recognizing the user with reference to user specific information according to the determined body type of the user in the case in which the user specific information including the body type, a weight, and massage mode setting information of the user is stored in advance when the former massage mode is ended; and automatically setting the massage mode of the thermal ceramic module according to the massage mode setting information of the recognized user.

A thermo-therapeutic apparatus and a method for controlling the same according to one embodiment of the present invention can provide massage at the same intensity for each body part regardless of a body type or a weight of the user in a predetermined desired intensity, and thus can maximize massage efficiency by adjusting an ascending and descending height of a ceramic member for each body part a body pressure of a user.

Further, since the present invention predicts a will of the user such as starting the massage, pausing the massage, ending the massage, or the like according to the body pressure and then automatically performs the massage, the user can select a massage mode without separate manipulation, and thus convenience for the user can be improved.

In addition, since the present invention recognizes the user according to body pressure distribution and a body type of the user, stores user specific information, and then uses stored massage operation setting to automatically perform massage setting when a particular user is recognized, the user can perform massage setting without separate manipulation, and thus convenience for the user can be further improved.

DETAILED DESCRIPTION OF THE INVENTION

Figure 1:
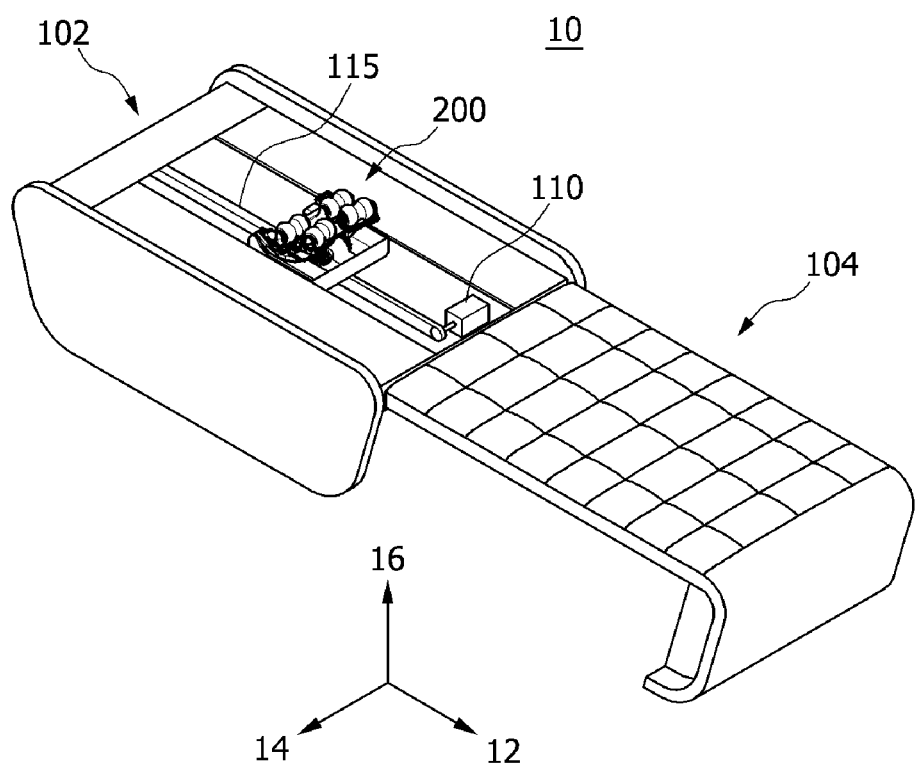
FIG. 1 is a schematic perspective view of a thermo-therapeutic apparatus according to one embodiment of the present invention.

Hereinafter, exemplary embodiments of the present invention will be described in detail with reference to the accompanying drawings which may allow one of ordinary skill in the art to easily perform the present invention. The present invention may be implemented in various forms and is not limited to the following embodiments. Components not related to the description are omitted in the drawings to clearly describe the present invention, and the same reference symbols are used for the same or similar components in the description.

Hereinafter, a thermo-therapeutic apparatus according to one embodiment of the present invention will be described in more detail with reference to the drawings. FIG. 1 is a schematic perspective view of a thermo-therapeutic apparatus according to one embodiment of the present invention.

Referring to FIG. 1, a thermo-therapeutic apparatus 10 is an apparatus capable of performing massage and thermotherapy using a thermal ceramic to a human body part. The thermo-therapeutic apparatus 10 includes an upper body 102, a lower body 104, and a thermal ceramic module 200.

The upper body 102 and the lower body 104 may be disposed in parallel. Hereinafter, a direction in which the upper body 102 and the lower body 104 are disposed in parallel refers to a first direction 12. When viewed from above, a direction perpendicular to the first direction 12 refers to a second direction 14. A direction perpendicular to both the first direction 12 and the second direction 14 refers to a third direction 16.

The upper body 102 has an empty space therein. The thermal ceramic module 200 may be placed in the empty space in the upper body 102. An upper surface of the upper body 102 may have a surface on which an upper body of the human may lie. The upper surface of the upper body 102 may be provided to be larger than an area of a back of the human.

The lower body 104 may move from the upper body 102 in a sliding method to overlap an upper portion of the upper body 102, or be disposed to be parallel to the upper body 102.

The thermal ceramic module 200 may perform the massage and thermotherapy for each human body part. The thermal ceramic module 200 may move in the upper body 102 along the first direction 12 by a conveyer 115 and a horizontal conveying motor 110 configured to drive the conveyer 115.

Accordingly, the thermal ceramic module 200 may be movable in the inner space of the upper body 102 to perform the thermotherapy to the human body part. As an example, when the human lies down on the thermal ceramic module 200, the thermal ceramic module 200 may perform the thermotherapy to a back or a cervical region.

Figure 2:
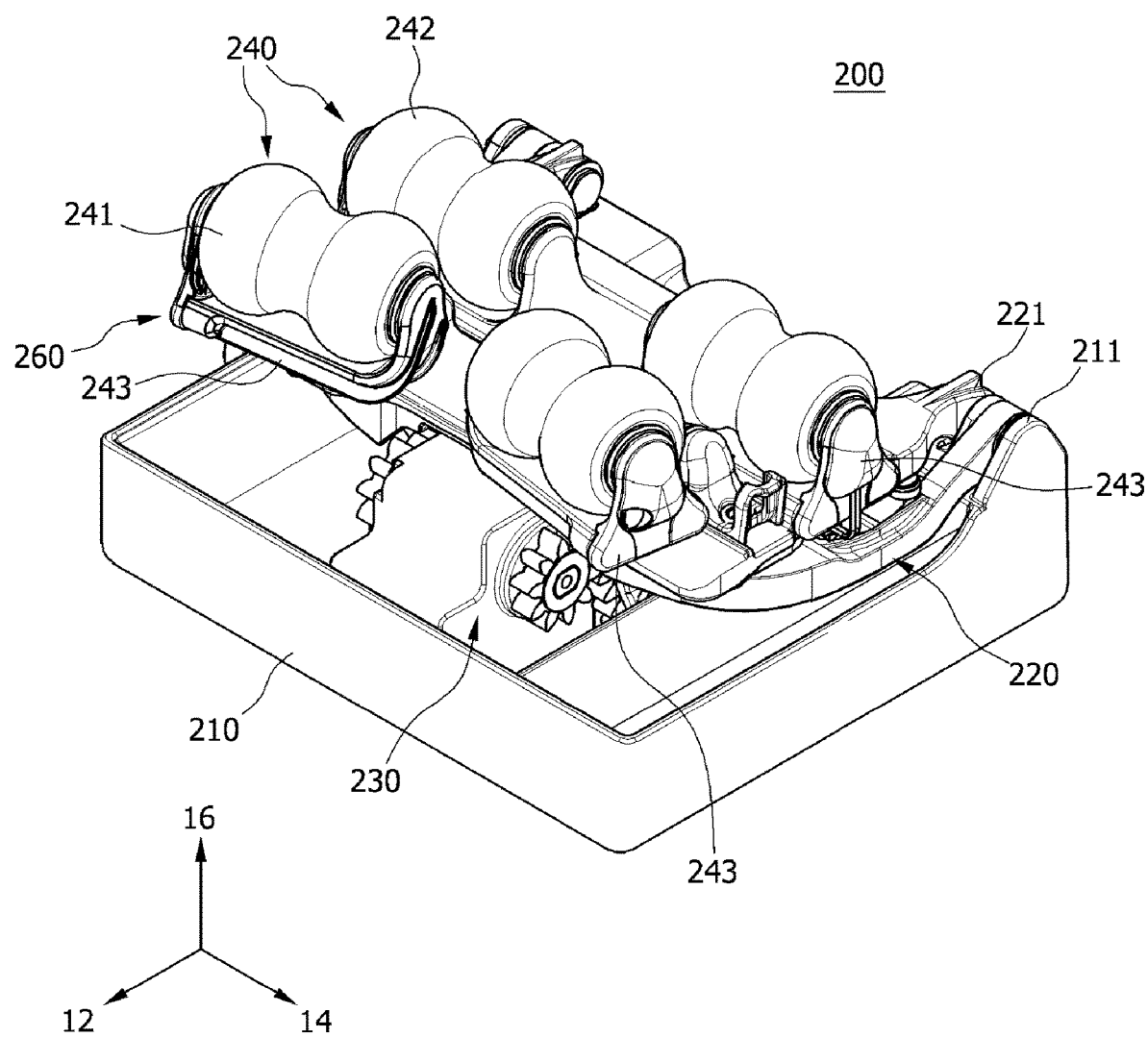
FIG. 2 is a perspective view of a thermal ceramic module in FIG. 1.
Figure 3:
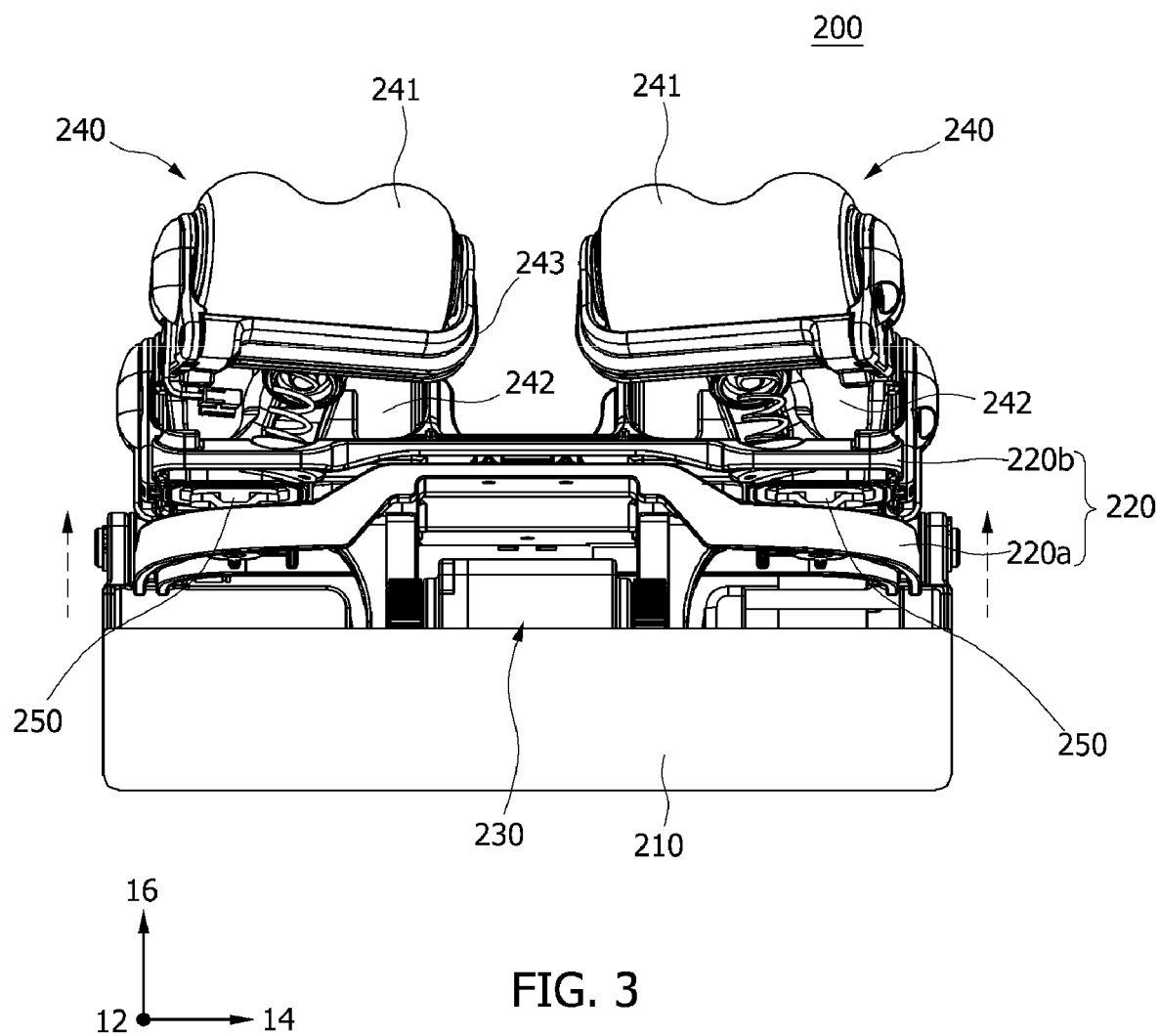
FIG. 3 is a front view of a state in which an ascending and descending driving part moves a supporting plate upward in the thermal ceramic module in FIG. 2.
Figure 4:
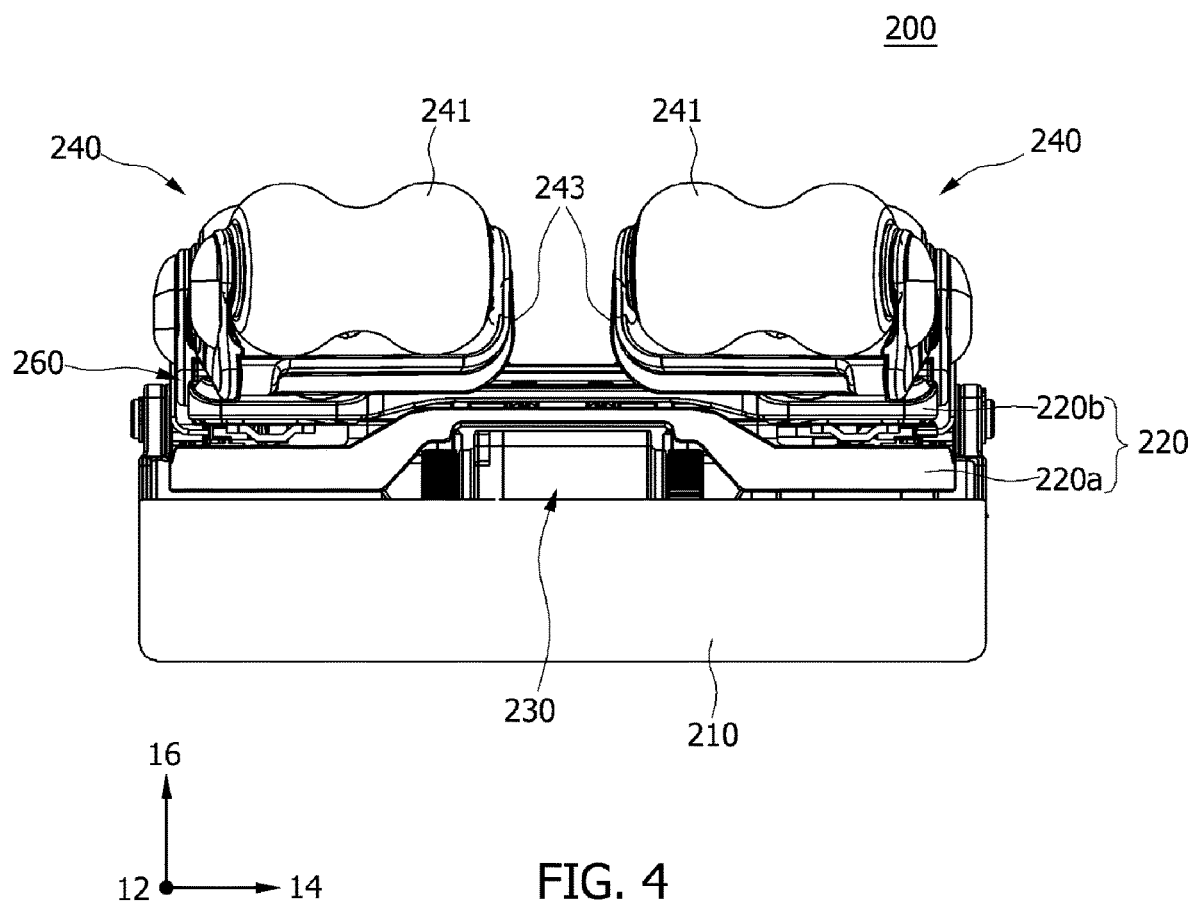
FIG. 4 is a front view of a state in which the ascending and descending driving part moves the supporting plate downward in the thermal ceramic module in FIG. 2.
Figure 5:
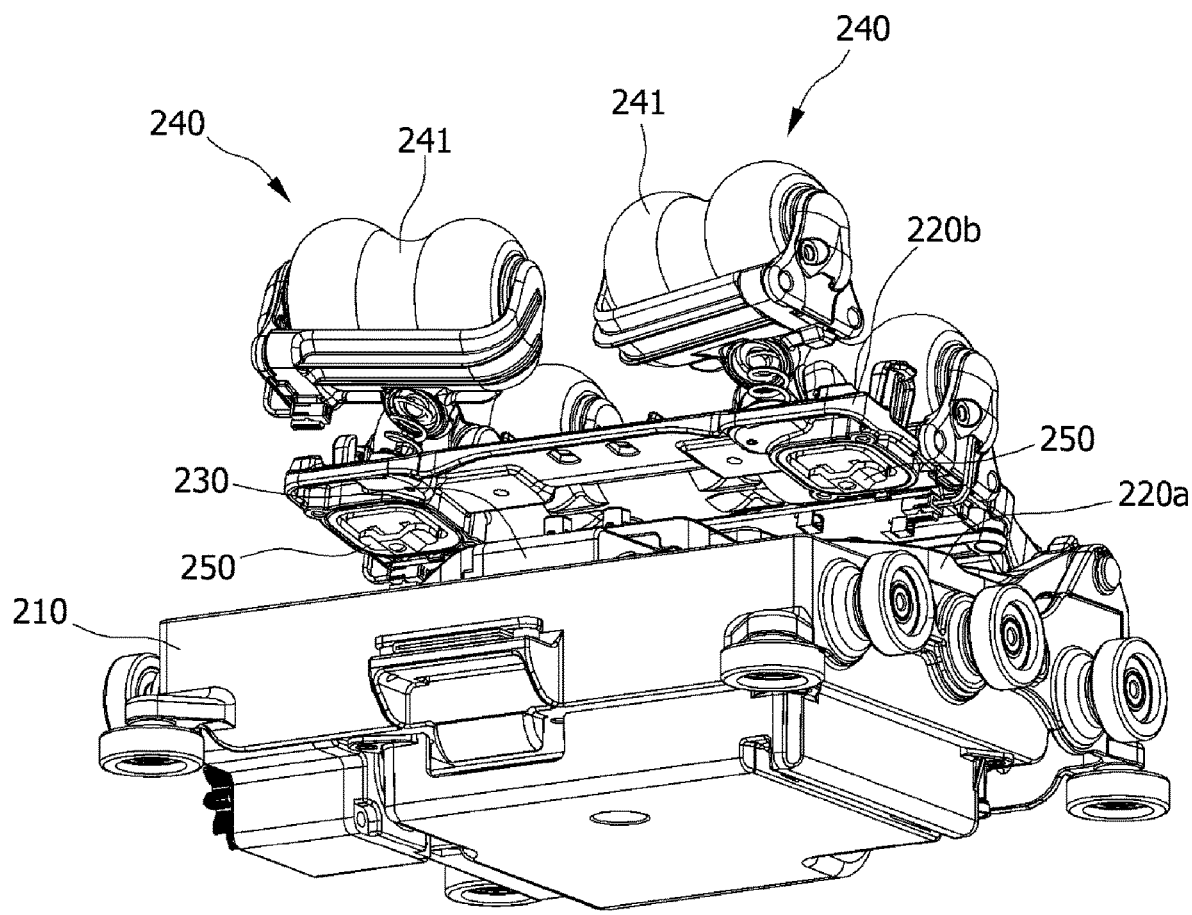
FIG. 5 is a perspective view of a first supporting plate and a second supporting plate viewed from below in a state of being separated from each other in the thermal ceramic module in FIG. 2.
Figure 6:
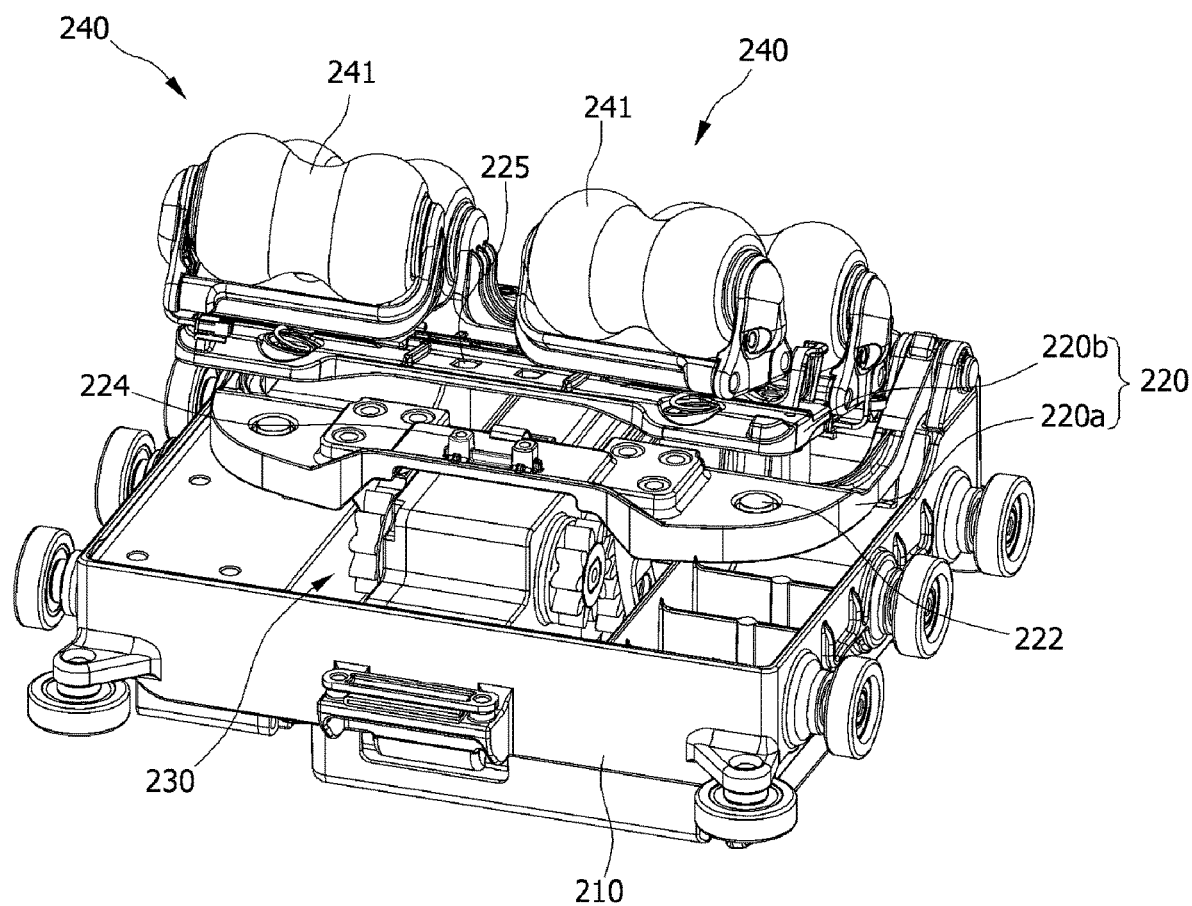
FIG. 6 is a perspective view of the first supporting plate and the second supporting plate viewed from above in the state of being separated from each other in the thermal ceramic module in FIG. 2.

FIG. 2 is a perspective view of the thermal ceramic module in FIG. 1, FIG. 3 is a front view of a state in which an ascending and descending driving part moves a supporting plate upward in the thermal ceramic module in FIG. 2, FIG. 4 is a front view of a state in which the ascending and descending driving part moves the supporting plate downward in the thermal ceramic module in FIG. 2, FIG. 5 is a perspective view of a first supporting plate and a second supporting plate viewed from below in a state of being separated from each other in the thermal ceramic module in FIG. 2, and FIG. 6 is a perspective view of the first supporting plate and the second supporting plate viewed from above in the state of being separated from each other in the thermal ceramic module in FIG. 2.

Referring to FIGS. 2 to 6, the thermal ceramic module 200 may include a body 210, a supporting plate 220, an ascending and descending driving part 230, ceramic members 240, weight sensors 250, and ceramic driving members 260.

The body 210 may include an empty space therein, and have a hexahedral shape. The body 210 has a shape of which an upper portion is open, but is not limited thereto, and may have various shapes.

Body supports 211 coupled to the supporting plate 220 may be formed in the body 210 so that the supporting plate 220 may rotate and move upward.

The pair of body supports 211 may be provided on an upper surface of the body 210 and formed to protrude inward in the body 210. The pair of body supports 211 may be located to be spaced apart from each other along the second direction 14. Each of the body supports 211 may be located at a rear end of the first direction 12 of each of the ceramic members 240 which will be described below.

The supporting plate 220 is located at an upper side of the third direction 16 of the body 210 and includes a first supporting plate 220a and a second supporting plate 220b. Here, the first supporting plate 220a may be disposed under the second supporting plate 220b and coupled to the ascending and descending driving part 230, and the ceramic members 240 may be coupled to the second supporting plate 220b.

Further, the supporting plate 220 may have support couplers 221 coupled to the body supports 211. When the supporting plate 220 moves upward, each of the support couplers 221 may act as a rotary shaft to move the supporting plate 220 upward. The pair of support couplers 221 may be formed and located at a rear end of the first direction 12 of the supporting plate 220.

Here, the first supporting plate 220a and the second supporting plate 220b may each include the support couplers 221. In this case, the first supporting plate 220a may be rotatable around the support couplers 221 when being moved upward by the ascending and descending driving part 230. Further, the second supporting plate 220b may also be rotatable around the support couplers 221, and thus may be spaced apart from the first supporting plate 220a.

In this case, the first supporting plate 220a may include pressing parts 222 corresponding to the weight sensors 250, which will be described below, in both sides of a surface thereof facing the second supporting plate 220b.

Further, the first supporting plate 220a may include a protrusion 224 at a center thereof, and the second supporting plate 220b may include a through port 225 at a location thereof corresponding to the protrusion 224. Here, the protrusion 224 may be inserted into the through port 225. In this case, the protrusion 224 may include a thread hole at a center thereof to insertion fix a coupling member thereto.

Accordingly, since the coupling member (not shown) is insertion fixed to the protrusion 224 in a state in which the protrusion 224 is inserted into the through port 225, the first supporting plate 220a and the second supporting plate 220b may be fixed.

The ascending and descending driving part 230 may move the supporting plate 220 in a third direction 16 which is a vertical direction on the basis of the body 210. The ascending and descending driving part 230 may be disposed in the inner space of the body 210, and coupled to the supporting plate 220.

As an example, the ascending and descending driving part 230 may move the supporting plate 220 in the third direction 16 using a gear, but is not limited thereto, and may be implemented using a cylindrical structure capable of vertically driving the supporting plate 220, or various devices.

The ceramic members 240 may come into contact with the human body part to perform the massage and thermotherapy. Each of the ceramic members 240 may be coupled to the supporting plate 220 and include a plurality of thermal ceramics 241 and 242.

Each of the plurality of thermal ceramics 241 and 242 may include a heating source therein to generate heat. Here, the heating source may be a lamp capable of generating light and heat, a positive temperature coefficient (PTC), a conductive hot wire, an electric heat wire, and the like, but is not limited thereto, and may be various configurations capable of generating only heat or both light and heat.

Each of the plurality of thermal ceramics 241 and 242 may be provided in a shape of which an outer surface is curved. As an example, in each of the plurality of thermal ceramics 241 and 242, both sides may have a spherical shape, and a center portion may have a cylindrical shape, and thus the ceramic members 240 may be formed in a shape similar to a dumbbell on the whole, but are not limited thereto, and may be formed in various shapes having a curved outer surface.

The plurality of thermal ceramics 241 and 242 may include at least the pair of first thermal ceramics 241 at a front side and the pair of second thermal ceramics 242 at a rear side along the first direction 12. The first thermal ceramics 241 and the second thermal ceramics 242 may be disposed to be spaced apart from each other along the second direction 14 at a predetermined distance.

The first thermal ceramics 241 and the second thermal ceramics 242 are disposed on the supporting plate 220, and may move to an upper side of the third direction 16 when the ascending and descending driving part 230 moves the supporting plate 220 to the upper side of the third direction 16.

Further, the first thermal ceramics 241 may move to the upper side of the third direction 16 by the ceramic driving members 260. That is, the first thermal ceramics 241 may move to the upper side or a lower side of the third direction 16 when only driven by the ceramic driving members 260 regardless of the movement of the supporting plate 220.

The second thermal ceramic 242 may be supported by a ceramic support 243. Here, the ceramic support 243 may be located at a lower side of the third direction 16 of the second thermal ceramic 242 and coupled to both side surfaces of the second thermal ceramic 243 to support a lower portion of the second thermal ceramic 242.

The weight sensors 250 are provided at locations corresponding to the pressing parts 222 of the first supporting plate 220a at both sides of a lower surface of the second supporting plate 220b. When a load is applied to each of the ceramic members 240, that is, when the ceramic members 240 come into contact with a body of a user and thus a pressure is applied to each of the ceramic members 240, the weight sensor 250 may sense a body pressure of the user.

The ceramic driving members 260 may move the first thermal ceramics 241 in the second direction 14 while also moving the first thermal ceramics 241 in the third direction 16. That is, the ceramic driving members 260 may move the pair of first thermal ceramics 241 in a diagonal direction in a plane formed by the second direction 14 and the third direction 16.

The thermo-therapeutic apparatus 10 according to the embodiment of the present invention may use the weight sensors 250 to provide the massage at the same pressure for a body part or a user. That is, by adjusting a driving height of the ascending and descending driving part 230 for the body part or the user at desired intensity of the massage, the thermo-therapeutic apparatus 10 may provide pressure so that each user feels the same pressure.

Figure 7:
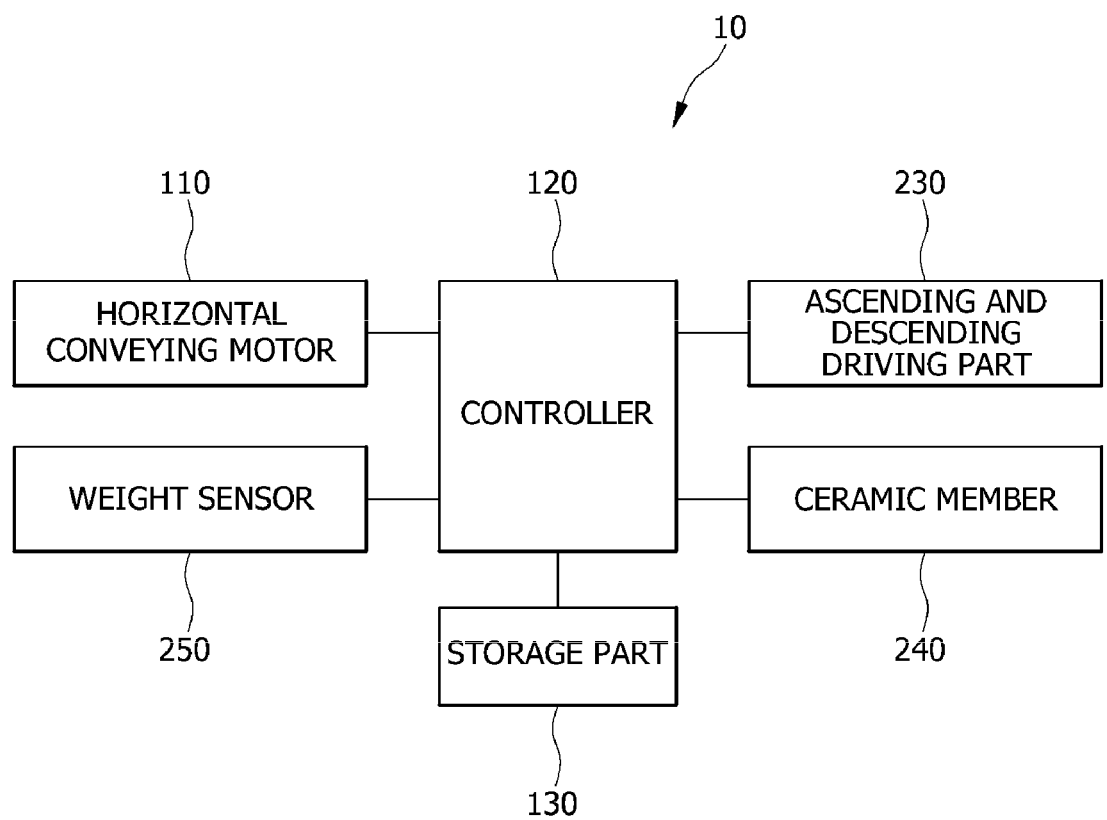
FIG. 7 is a block diagram illustrating the thermo-therapeutic apparatus according to the embodiment of the present invention.
Figure 8:
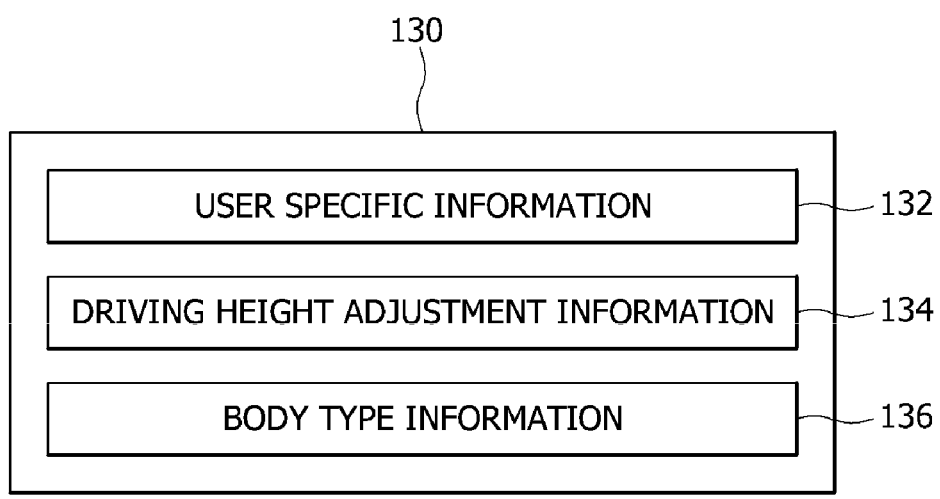
FIG. 8 is a view illustrating a detailed block diagram of a storage part in FIG. 7.

Hereinafter, a configuration for adjusting the driving height of the ascending and descending driving part 230 using the weight sensors 250 will be described with reference to FIGS. 7 and 8. FIG. 7 is a block diagram illustrating the thermo-therapeutic apparatus according to the embodiment of the present invention, and FIG. 8 is a view illustrating a detailed block diagram of a storage part in FIG. 7.

The thermo-therapeutic apparatus 10 according to one embodiment of the present invention includes a controller 120 configured to control the above described horizontal conveying motor 110, the ascending and descending driving part 230 included in the thermal ceramic module 200, and the ceramic members 240 using the weight sensors 250, and a storage part 130. Here, the controller 120 may retrieve information for controlling from the storage part 130, or store setting information of a current massage mode in the storage part 130.

The controller 120 controls setting and performance of a massage mode of the thermal ceramic module 200. That is, the controller 120 controls the ascending and descending driving part 230 to perform the massage by the ceramic members 240 while moving the thermal ceramic module 200 by controlling the horizontal conveying motor 110 according to setting of the user or automatic setting by user recognition which will be described below.

In this case, the controller 120 may control the driving height of the ascending and descending driving part 230 according to the body pressure of the user sensed by the weight sensors 250 on the basis of a predetermined desired intensity. Here, since a body pressure varies for each body part according to a body type of the user, when the driving height of the ascending and descending driving part 230 is controlled to be uniform according to a desired intensity, the body pressure felt by the user for each body part varies, and thus, in the present invention, the controller 120 may provide the same pressure for each body part to the user by adjusting the driving height of the ascending and descending driving part 230.

To this end, the controller 120 may control the driving height of the ascending and descending driving part 230 using driving height adjustment information according to the body pressure sensed by the weight sensors 250 on the basis of reference height information of the ascending and descending driving part 230 set for a primarily set desired intensity. Here, the reference height information may be driving height information of the ascending and descending driving part 230 according to the desired intensity, and the driving height adjustment information may be information previously calculated for the body pressure according to a body type of the user scanned at a particular desired intensity as described below. That is, the controller 120 may adjust the driving height according to the desired intensity for the body pressure according to the body type of the user to calculate the driving height adjustment information.

As an example, on the basis of reference height according to the desired intensity, the driving height may be increased and decreased according to a body pressure for each of the cervical vertebrae, the thoracic vertebrae, the lumbar vertebrae, and the sacral vertebrae according to the body type of the user recognized by scanning. In this case, by lowering the driving height of the ascending and descending driving part 230 for each of the thoracic vertebrae and the sacral vertebrae to which the relatively high body pressure is applied, as the supporting plate 220 descends, the ceramic members 240 may also descend to decrease the pressure, and thus the pressure felt by the user may be decreased.

Further, by elevating the driving height of the ascending and descending driving part 230 for each of the cervical vertebrae and the lumbar vertebrae to which the relatively low body pressure is applied, as the supporting plate 220 ascends, the ceramic members 240 may also ascend to increase the pressure, and thus the pressure felt by the user may be increased.

As described above, the thermo-therapeutic apparatus 10 may control the pressure to be equally applied to the body by the ceramic members 240 regardless of the body type or a weight by adjusting the driving height of the ascending and descending driving part 230 according to the body pressure which varies for each body part of the same user, and accordingly, the user may receive the massage at the same pressure.

Further, even in a case of different users, particularly, users having the same body type but different weights, the thermo-therapeutic apparatus 10 may provide the massage at the same pressure to the users by adjusting the driving height of the ascending and descending driving part 230 according to various body pressures.

In addition, the controller 120 may determine whether the user is ready to receive the massage according to a sensing result sensed by the weight sensors 250 and control the thermal ceramic module 200 so that the massage mode is automatically started.

As an example, the controller 120 may determine whether a predetermined time passes without a predetermined change of the pressure after the weight sensors 250 sense a pressure greater than or equal to a first reference pressure, and determine that the user is lying on the thermo-therapeutic apparatus 10 and waiting to receive the massage when the predetermined time passes.

In this case, when the pressure is greater than or equal to the first reference pressure but varies, the controller 120 may initialize the time which has passed. As an example, although the user lies on the thermo-therapeutic apparatus 10, and thus the weight sensors 250 sense the pressure greater than or equal to the first reference pressure, since the user is in a state of not being ready to receive the massage when moving into a posture to receive the massage, the controller 120 may initialize the time which has passed. That is, the controller 120 may determine whether the time passes only when the pressure is greater than or equal to the first reference pressure and does not vary.

As a result, the controller 120 may determine that the user is ready to receive the massage only when a state in which the pressure is greater than or equal to the first reference pressure and does not vary is maintained for a predetermined time.

Here, the first reference pressure may be a pressure to a degree by which the user may be known to lie on the upper body 102, in a state in which the thermal ceramic module 200 is located at one side in the upper body 102 before the massage mode of the thermal ceramic module 200 is started.

In this case, the controller 120 may control the horizontal conveying motor 110, the ascending and descending driving part 230, and the ceramic members 240 according to a mode set to automatically start the massage mode of the thermal ceramic module 200.

Further, the controller 120 may determine whether the user desires to stop the massage according to the sensing result sensed by the weight sensors 250 while the thermal ceramic module 200 performs the massage mode and may control the thermal ceramic module 200 so that the massage mode is automatically paused.

As an example, the controller 120 may determine that the user gets up from thermo-therapeutic apparatus 10 during the massage when a predetermined time passes after the weight sensors 250 senses a pressure less than or equal to a second reference pressure.

Here, the second reference pressure is a pressure to a degree by which the user may be known to get up from the upper body 102, in a state in which the thermal ceramic module 200 moves in the upper body 102 while the massage mode of the thermal ceramic module 200 is performed, and the second reference pressure may have a value, as an example, less than or equal to that of the first reference pressure. However, the second reference pressure is not limited thereto and may have a value greater than that of the first reference pressure.

In this case, the controller 120 may stop to control the horizontal conveying motor 110, the ascending and descending driving part 230, and the ceramic members 240 so that the massage mode of the thermal ceramic module 200 is automatically paused.

Further, the controller 120 may store a location of the body part at which the massage is stopped in the storage part 130. That is, on the basis of the location and the body pressure sensed at a location at which the massage is paused, the controller 120 may determine a body part corresponding to body pressure distribution according to the body type of the user recognized by scanning and store a location in the determined body part as a previous massage location.

In this case, when performing the massage again after pausing, the controller 120 may control the thermal ceramic module 200 to continuously perform the massage from the body part at which the massage is paused on the basis of posture information stored before the massage is paused. That is, in a case in which a posture of the user is changed in a process in which the massage is paused during the performance and thus the user gets out of the thermo-therapeutic apparatus 10, or gets up and then lies down again, since a position of the vertebrae is changed and thus the body pressure distribution may be changed, the user may feel uncomfortable when the massage is performed according to the adjustment information of the previously adjusted driving height.

Accordingly, the controller 120 may control the thermal ceramic module 200 to search for a body part when performing the massage again, and perform the massage again from the body part. In this case, since the thermal ceramic module 200 moves to a location which is the same as that of the body pressure corresponding to the body part at which the massage is paused, the controller 120 may perform the massage again in the same manner as the previous massage.

Further, in a state in which the thermal ceramic module 200 pauses the performance of the massage mode, the controller 120 may determine whether the user desires to end the massage according to whether a predetermined time passes, and control the thermal ceramic module 200 so that the massage mode is automatically ended.

As an example, the controller 120 may determine that the user desires to arbitrarily end the massage mode when the predetermined time passes after the massage mode is paused.

In this case, the controller 120 may cease to control the horizontal conveying motor 110, the ascending and descending driving part 230, and the ceramic member 240 so that the massage mode of the thermal ceramic module 200 is automatically ended.

Further, the controller 120 may store setting information of a current massage mode in the storage part 130 as information of the user when the massage mode of the thermal ceramic module 200 is ended. In this case, the controller 120 may control user specific information 132 stored in the storage part 130 so that the user specific information 132 is updated with the setting information of the current massage mode. Here, the setting information of the current massage mode may include finally used mode information, temperature information, and intensity information.

Accordingly, since the massage may be automatically performed without separate manipulation by the user for starting, pausing, and ending the massage, and information of a previous massage mode may be continuously updated, convenience for the user may be improved.

Further, the controller 120 may determine the body type of the user according to at least one of the body pressure distribution of the user according to the sensing result sensed by the weight sensors 250 and a current variation amount of the horizontal conveying motor 110. Here, in a process in which the thermal ceramic module 200 moves during the massage, since a pressure added from the body of the user to the thermal ceramic module 200 varies according to a location of the vertebrae of the user, the controller 120 may determine the body type of the user such as a length of the vertebrae, or the like according to the body pressure distribution of the user.

In addition, since the current variation amount of the horizontal conveying motor 110 increases when the pressure added to the thermal ceramic module 200 becomes greater, and decreases when the pressure becomes lower, the controller 120 may determine the body type of the user such as the length of the vertebrae, or the like according to the current variation amount of the horizontal conveying motor 110.

In this case, the controller 120 may determine the body type of the user with reference to the body type information according to at least one of body pressure distribution of the user for each body part, and the current variation amount of the horizontal conveying motor 110. Here, the body type information may be information previously calculated by classifying at least one of the body pressure distribution of the user for each body part and the current variation amount of the horizontal conveying motor 110 according to standard vertebrae information.

Further, when user specific information 132 of previous use of the thermo-therapeutic apparatus 10 is stored, the controller 120 may recognize a current user according to the determined body type of the user.

Operations for determining the body type of the user and recognizing the user may be performed first when the thermal ceramic module 200 starts the massage mode. In this case, when the user uses the thermo-therapeutic apparatus 10 for the first time or the user specific information 132 is not previously stored, the body type of the user may be stored in the user specific information 132.

Further, when the user is recognized before the massage mode is performed, the controller 120 may automatically set the massage mode of the thermal ceramic module 200 with reference to the user specific information 132 in the storage part 130 according to massage mode setting information of the user. Here, the massage mode setting information may include a temperature, an intensity and a massage pattern.

Accordingly, since the thermo-therapeutic apparatus 10 may recognize the user according to a human body scan before performing the massage and automatically set the massage mode to a predetermined massage mode without particular manipulation by the user, the convenience for the user may be further improved.

The user specific information 132, driving height adjustment information 134, and body type information 136 may be stored in the storage part 130.

The user specific information 132 may include the body type, the weight, and the massage mode setting information of the user. Here, the massage mode setting information may include finally used mode information, the temperature information, and the intensity information. When the user using the thermo-therapeutic apparatus 10 is registered, the user specific information 132 may be updated each time in which the thermo-therapeutic apparatus 10 ends after being used.

As described above, the driving height adjustment information 134 may include reference height information of the ascending and descending driving part 230, and the driving height adjustment information according to the body pressure sensed on the basis of the reference height information.

The body type information 136 may be body type information corresponding to the at least one of the body pressure distribution and the current variation amount of the horizontal conveying motor 110. Here, the body type information may be the vertebrae information such as the length of the vertebrae according to the body pressure distribution and the current variation amount of the horizontal conveying motor 110 or the like classified according to the standard vertebrae information.

Figure 9:
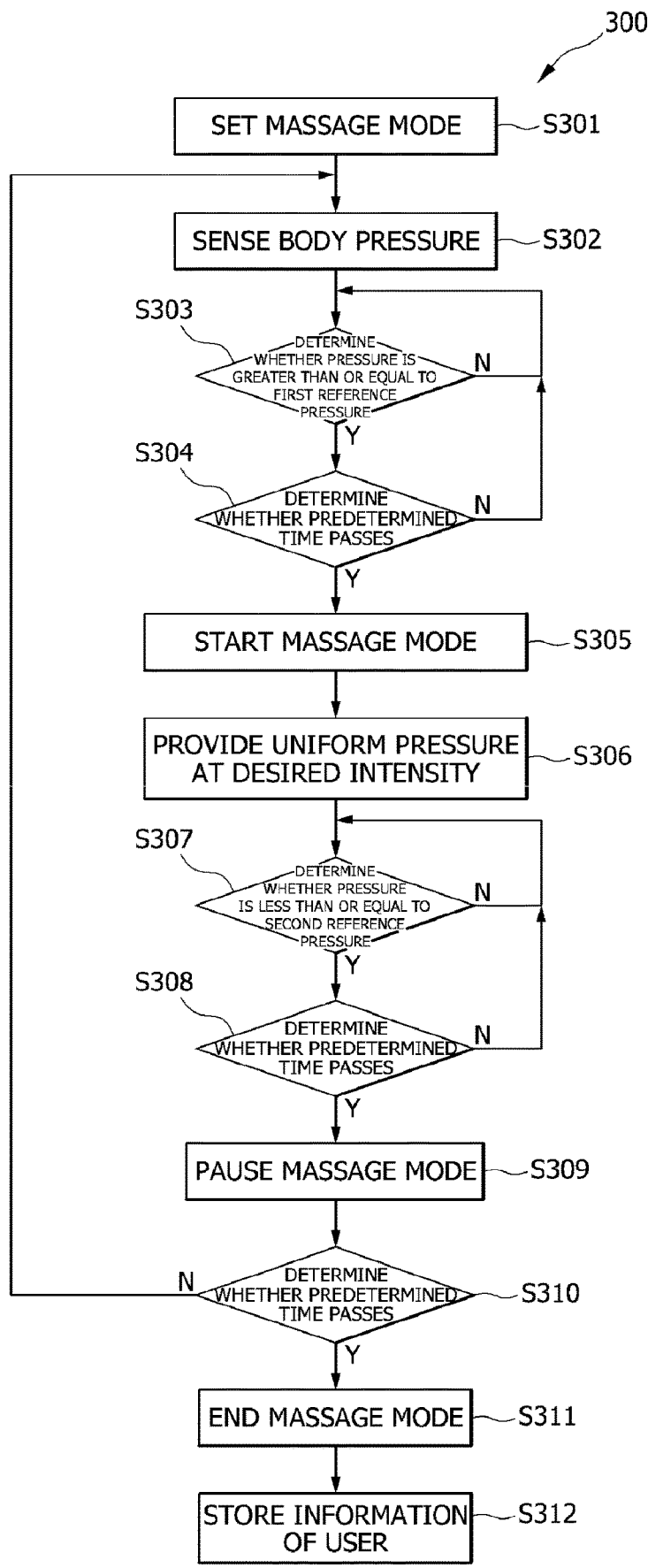
FIG. 9 is a flow chart illustrating a method for controlling the thermo-therapeutic apparatus according to the embodiment of the present invention.
Figure 10:
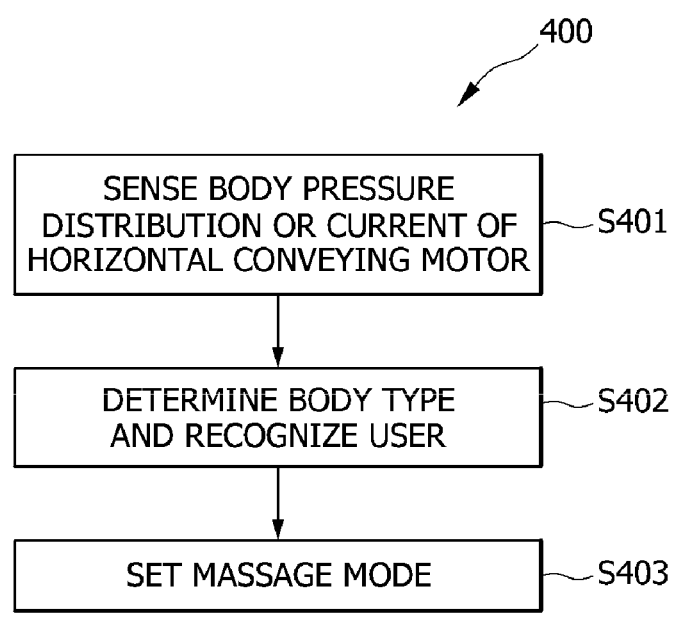
FIG. 10 is a flow chart illustrating one example of starting a massage mode in FIG. 9.

Hereinafter, a method for controlling the thermo-therapeutic apparatus in the present invention will be described below in detail with reference to FIGS. 9 and 10. FIG. 9 is a flow chart illustrating a method for controlling the thermo-therapeutic apparatus according to the embodiment of the present invention.

A method 300 for controlling the thermo-therapeutic apparatus according to the embodiment of the present invention includes setting a massage mode (S301), automatically starting the massage mode by sensing the pressure in the weight sensors 250 (S302 to S305), providing a uniform pressure according to the desired intensity (S306), and automatically pausing or ending the massage mode (S307 to S312).

In more detail, as shown in FIG. 9, the massage mode of the thermal ceramic module 200 may be automatically or manually set first (S301). In this case, when the user uses the thermo-therapeutic apparatus 10 for the first time, or user setting is not set before, the user may directly set the massage mode.

Further, a body pressure added to the weight sensors 250 may be sensed (S302). In this case, when the ceramic members 240 come into contact with the body of the user, and thus the pressure is applied, the weight sensors 250 may sense the pressure and then sense the body pressure of the user.

In addition, it is determined whether the sensed body pressure is greater than or equal to the first reference pressure (S303), and when the body pressure is lower than or equal to the first reference pressure, the user is determined to be not on the thermo-therapeutic apparatus 10 and the thermo-therapeutic apparatus 10 waits until the body pressure becomes greater than or equal to the first reference pressure.

As a result of the determination in S303, when the sensed body pressure is determined to be greater than or equal to the first reference pressure, whether a predetermined time passes without a predetermined change of the pressure is determined (S304), and when the predetermined time does not pass in a state in which the sensed body pressure is greater than or equal to the first reference pressure, the user is determined to be not ready to receive the massage and the thermo-therapeutic apparatus 10 waits in standby until the condition is satisfied.

In this case, when the pressure is greater than or equal to the first reference pressure but varies, the time which has passed may be initialized. As an example, although the user lies on the thermo-therapeutic apparatus 10, and thus the pressure greater than or equal to the first reference pressure is sensed, since the user is in the state of not being ready to receive the massage when moving into a posture to receive the massage, the time which has passed may be initialized. That is, whether the time passes may be determined only when the pressure is greater than or equal to the first reference pressure and does not vary.

As a result of the determination in S304, when the predetermined time is determined to pass without a predetermined change of the pressure in the state in which the body pressure is greater than or equal to the first reference pressure, the user may be determined to be ready to receive the massage and the massage mode of the thermal ceramic module 200 may be started (S305).

Here, when the pressure is greater than or equal to the first reference pressure and varies, since the time which has passed is initialized, the user may be determined to be ready to receive the massage only when the state in which the pressure is greater than or equal to the first reference pressure and does not vary is maintained for the predetermined time.

In this case, when the user setting is stored, as described below with reference to FIG. 10, by scanning a human body of the user, adjusting the driving height according to a set desired intensity may be performed.

Further, since the supporting plate 220 ascends and descends through the ascending and descending driving part 230 according to the set desired intensity while the thermal ceramic module 200 horizontally moves in the upper body 102 by driving of the horizontal conveying motor 110, the body of the user may be massaged by the ceramic members 240.

As described above, by controlling the driving height of the ascending and descending driving part 230 using the driving height adjustment information according to the body pressure of the user sensed by the weight sensors 250 on the basis of the predetermined desired intensity while the massage mode of the thermal ceramic module 200 is performed, the pressure may be uniformly provided at the desired intensity (S306).

In this case, the driving height of the ascending and descending driving part 230 for each body part may be controlled with reference to the driving height adjustment information calculated according to the body pressure sensed by the weight sensors 250 when the human body is scanned. Here, reference height information of the ascending and descending driving part 230 for the desired intensity, and the driving height adjustment information 134 according to the body pressure sensed on the basis of the reference height information may be stored in advance in the storage part 130 to be provided later.

As described above, by adjusting the driving height of the ascending and descending driving part 230 according to the pressure which varies for each body part of the user, the user may receive the massage at the same pressure for each body part.

Further, it is determined whether the weight sensors 250 sense the pressure less than or equal to a second reference pressure (S307), and when a pressure greater than or equal to the second reference pressure is sensed, the user may be determined to desire to continuously receive the massage, and thus the previous massage mode may be continuously performed until the pressure lower than or equal to the second reference pressure is sensed.

As a result of the determination in S307, when the weight sensors 250 sense the pressure less than or equal to the second reference pressure, whether the predetermined time passes is determined (S308), and when the predetermined time does not pass in a state in which the sensed body pressure is lower than or equal to the second reference pressure, the user may be determined to only temporarily change the posture and desire to continuously receive the massage, and thus the massage mode may be continuously performed until the condition is satisfied.

As a result of the determination in S308, when the predetermined time is determined to pass in the state in which the sensed body pressure is less than or equal to the second reference pressure, the user may be determined to desire to arbitrarily stop or pause the massage, and thus the massage mode may be automatically paused (S309).

In this case, the user may store a location of the body part at which the massage is stopped in the storage part 130 on the thermo-therapeutic apparatus 10. That is, on the basis of the body pressure sensed at a location at which the massage is paused, the location of the body part corresponding to the body pressure distribution according to the body type of the user recognized by scanning may be determined, and then stored as the previous massage location.

Further, it is determined whether the predetermined time passes (S310), and when the predetermined time is determined not to pass, S302 to S309 may be repeatedly performed to restart the massage mode by returning to S302 and determining whether the user lies on the thermo-therapeutic apparatus 10 to receive the massage again.

In this case, the thermo-therapeutic apparatus 10 may continuously perform massage from the body part at which the massage is paused on the basis of the posture information stored before the massage is paused. That is, in the case in which the posture of the user is changed in the process in which the massage is paused during the performance and thus the user gets up from the thermo-therapeutic apparatus 10, or gets up and then lies down again, since the position of the vertebrae is changed and thus the body pressure distribution may be changed, the user may feel uncomfortable when the massage is performed according to the driving height adjustment information of the previously adjusted driving height.

Accordingly, the massage may be performed again from the body part by searching for the body part at which the massage is paused. In this case, since the thermal ceramic module 200 moves to the location the same as that of the body pressure corresponding to the body part at which the massage is paused, the massage may be performed again in the same manner as the previous massage.

As a result of the determination in S310, when the predetermined time is determined to pass, the user may be determined to complete receiving the massage or desire to end the massage mode by stopping, and then the massage mode of the thermal ceramic module 200 may be ended (S311).

Further, the setting information of the current massage mode may be stored in the storage part 130 as the information of the user upon ending the massage mode (S312). Here, the setting information of the current massage mode may include the finally used mode information, the temperature information, and the intensity information. In this case, when the user specific information 132 is previously stored, the user specific information 132 may be updated with the setting information of the current massage mode at an end of every massage mode.

Accordingly, since the massage may be automatically performed without the separate manipulation by the user for starting, pausing, and ending the massage, and the information of the previous massage mode may be continuously updated, convenience for the user may be improved.

Automatic setting of the massage mode will be described in detail with reference to FIG. 10. FIG. 10 is a flow chart illustrating one example of starting the massage mode in FIG. 9.

First, at least one of the body pressure distribution through the human body scan and a current variation amount of the horizontal conveying motor 110 may be sensed (S401). In this case, since the horizontal conveying motor 110 horizontally moves the thermal ceramic module 200 in the upper body 102, and thus the ceramic members 240 press the human body, the weight sensor 250 may sense the body pressure of the user or the current variation amount of the horizontal conveying motor 110 in a process of driving and horizontally moving the thermal ceramic module 200.

Further, the body type of the user may be determined with reference to the body type information provided in advance according to at least one of the body pressure distribution of the user according to the sensing result sensed by the weight sensors 250, and the current variation amount of the horizontal conveying motor 110, and the user may be recognized with reference to the user specific information 132 according to the determined body type of the user (S402).

Here, the body type information 136 corresponding to at least one of the body pressure distribution and the current variation amount of the horizontal conveying motor 110 may be classified according to the standard vertebrae information, and stored in the storage part 130 in advance to be provided.

In this case, when the user uses the thermo-therapeutic apparatus 10 for the first time or the user specific information 132 is not stored before, the body type of the user may be stored in the user specific information 132. Further, in this case, setting the massage mode (S403) which will be described below may be omitted.

In addition, the massage mode of the thermal ceramic module 200 may be automatically set with reference to the massage mode setting information of the recognized user (S403). The automatic setting may be restrictively performed only when the user specific information 132 is stored in advance.

Accordingly, since the thermo-therapeutic apparatus 10 may recognize the user according to the human body scan before performing the massage and automatically set the massage mode to the predetermined massage mode without the particular manipulation by the user, the convenience for the user may be further improved.

The above described methods may be implemented by the controller 120 of the thermo-therapeutic apparatus 10 as shown in FIG. 7 and, notably, implemented by software programs configured to perform the steps, and in this case, the programs may be stored in a recording medium readable by a computer or transmitted by computer data signals mixed with a carrier wave in transmission media or a network.

In this case, the record medium readable by the computer includes all kinds of recording devices in which data readable by a computer system is stored, for example a ROM, a RAM, a CD-ROM, a DVD-ROM, a DVD-RAM, a magnetic tape, a floppy disk, a hard disk, an optical data storage device, etc.

Although one embodiment of the present invention is described above, the spirit of the present invention is not limited to the embodiment shown in the description, and although those skilled in the art may provide other embodiments due to addition, change, or removal of the components within the scope of the same spirit of the present invention, the above embodiments are also included in the scope of the spirit of the present invention.

The invention claimed is:

1. A thermo-therapeutic apparatus comprising:
a thermal ceramic module including a body, a first supporting plate located on the body, a second supporting plate located on the first supporting plate, an ascending and descending driving part coupled to a lower portion of the first supporting plate and configured to move the first supporting plate in a vertical direction with respect to of the body, and a ceramic member coupled to the second supporting plate;
a weight sensor provided on a lower surface of the second supporting plate to sense a body pressure of a user; and
a controller configured to control setting and performance of a massage mode of the thermal ceramic module, wherein the controller controls a driving height of the ascending and descending driving part according to the body pressure of the user sensed by the weight sensor, to provide the same pressure to the user through the ceramic member on the basis of a predetermined desired intensity,
wherein the controller controls the thermal ceramic module so that the massage mode is automatically started when a predetermined time passes without a predetermined change of the pressure after the weight sensor senses a pressure greater than or equal to a first reference pressure, and re-initializes the time which has passed when the pressure varies in the predetermined time,
wherein the controller controls the thermal ceramic module so that the massage mode is automatically paused while the massage mode is performed when a predetermined time passes after the weight sensor senses a pressure lower than or equal to a second reference pressure which is lower than the first reference pressure, and stores a paused location of the thermal ceramic module relative to the user's body and the sensed pressure by the weight sensor when the massage mode is paused,
wherein the controller searches the user's body and controls a movement of the thermal ceramic module to a location which is the same as the stored paused location relative to the user's body so that the massage mode is restarted at the paused location when the weight sensor senses a pressure greater than or equal to the first reference pressure in a predetermined time after the massage mode is paused.

2. The thermo-therapeutic apparatus of claim 1, further comprising a storage part in which driving height adjustment information of the ascending and descending driving part corresponding to the predetermined desired intensity based on the body pressure of a body part as reference height information is stored,
wherein the controller controls the driving height of the ascending and descending driving part with reference to the driving height adjustment information according to the body pressure sensed by the weight sensor.

3. The thermo-therapeutic apparatus of claim 1, wherein the controller determines whether the predetermined time passes after the massage mode is paused, and controls the thermal ceramic module so that the massage mode is automatically ended when the predetermined time passes.

4. The thermo-therapeutic apparatus of claim 1, further comprising a storage part in which user specific information including a body type, a weight, and massage mode setting information of the user is stored,
wherein the controller stores current massage mode setting information in the storage part as the user specific information when the massage mode of the thermal ceramic module is ended.

5. The thermo-therapeutic apparatus of claim 1, further comprising:
a horizontal conveying motor configured to horizontally drive the thermal ceramic module; and
a storage part configured to store body type information corresponding to at least one of body pressure distribution and a current variation amount of the horizontal conveying motor,
wherein the controller determines a body type of the user with reference to the body type information according to body pressure distribution of the user on the basis of a sensing result sensed by the weight sensor for a body part and a current variation amount of the horizontal conveying motor according to a location.

6. The thermo-therapeutic apparatus of claim 5, wherein:
the storage part stores user specific information including the body type, a weight, and massage mode setting information of the user; and
the controller recognizes the user with reference to the user specific information according to the determined body type of the user and automatically sets the massage mode of the thermal ceramic module according to massage mode setting information of the recognized user.

7. A method for controlling a thermo-therapeutic apparatus comprising:
setting a massage mode of a thermal ceramic module including a body, a first supporting plate located on the body, a second supporting plate located on the first supporting plate, an ascending and descending driving part coupled to a lower portion of the second supporting plate and configured to move the first supporting plate in a vertical direction with respect to the body, and a ceramic member coupled to the second supporting plate;
sensing a body pressure of a user through a weight sensor provided on a lower surface of the second supporting plate;
a first determining operation which determines whether a predetermined time passes without a predetermined change of the pressure after the weight sensor senses a pressure greater than or equal to a first reference pressure;
initializing the time which has passed when the pressure varies;
automatically starting the massage mode of the thermal ceramic module only when a state in which the pressure is greater than or equal to the first reference pressure and does not vary for the predetermined time;
controlling performance of the massage mode of the thermal ceramic module, wherein a driving height of the ascending and descending driving part is controlled according to the body pressure of the user sensed by the weight sensor to provide the same pressure to the user through the ceramic member on the basis of a predetermined desired intensity,
a second determining operation which determines whether a predetermined time passes after the weight sensor senses a pressure lower than or equal to a second reference pressure which is lower than the first reference pressure while the massage mode is performed;
automatically pausing the massage mode of the thermal ceramic module when the predetermined time passes;
storing a paused location of the thermal ceramic module relative to the user's body and the sensed pressure by the weight sensor when the massage mode is paused; and
searching the user's body and controlling a movement of the thermal ceramic module to a location which is the same as the stored paused location relative to the user's body so that the massage mode is restarted at the paused location when the weight sensor senses a pressure greater than or equal to the first reference pressure in a predetermined time after the massage mode is paused.

8. The method for controlling a thermo-therapeutic apparatus of claim 7, further comprising:
providing reference height information of the ascending and descending driving part according the desired intensity,
wherein the controlling includes calculating driving height adjustment information according to the body pressure sensed on the basis of the reference height information and controlling the driving height of the ascending and descending driving part with reference to the driving height adjustment information according to the body pressure sensed by the weight sensor.

9. The method for controlling a thermo-therapeutic apparatus of claim 7, further comprising:
a third determining operation which determines whether a predetermined time passes after the massage mode is paused; and
automatically ending the massage mode of the thermal ceramic module when the predetermined time passes.

10. The method for controlling a thermo-therapeutic apparatus of claim 7, further comprising:
providing body type information corresponding to at least one of body pressure distribution and a current variation amount of a horizontal conveying motor configured to horizontally drive the thermal ceramic module;
sensing at least one of a body pressure for a body part of the user and a current change of the horizontal conveying motor according to a location;
determining a body type of the user with reference to the body type information according to body pressure distribution of the user on the basis of a sensing result sensed by the weight sensor and a current variation amount of the horizontal conveying motor according to a location;
recognizing the user with reference to user specific information according to the determined body type of the user in the case in which the user specific information including the body type, a weight, and massage mode setting information of the user is stored in advance when the former massage mode is ended; and
automatically setting the massage mode of the thermal ceramic module according to the massage mode setting information of the recognized user.

* * * * *